United States Patent [19]
Levenson

[11] Patent Number: 5,647,824
[45] Date of Patent: Jul. 15, 1997

[54] WEIGHT LIFTER'S BELT INCORPORATING STRAP RATCHET AND NYLON STRAP

[76] Inventor: Bruce Adam Levenson, PSC 2, Box 10536, APO, AE, 09012

[21] Appl. No.: 547,801

[22] Filed: Oct. 25, 1995

[51] Int. Cl.⁶ .................................................. A61F 5/37
[52] U.S. Cl. .................................................. 482/92; 2/311
[58] Field of Search .............................. 602/19; 482/93, 482/106, 92; 2/44, 311, 320, 338; 119/770; 182/3, 4

[56] References Cited

U.S. PATENT DOCUMENTS

| | | | |
|---|---|---|---|
| 3,466,668 | 9/1969 | Ochiai | 2/338 X |
| 4,348,774 | 9/1982 | Woodson | 2/338 |
| 4,509,214 | 4/1985 | Shea | 2/322 |
| 4,541,152 | 9/1985 | DiMarco et al. | 24/271 |
| 4,685,668 | 8/1987 | Newlin . | |
| 4,689,833 | 9/1987 | Daniels | 2/322 |
| 4,802,667 | 2/1989 | Altner . | |
| 4,905,993 | 3/1990 | Barone . | |
| 4,964,401 | 10/1990 | Taigen . | |
| 4,968,027 | 11/1990 | Anderson et al. . | |
| 5,065,773 | 11/1991 | Jackson et al. | 128/876 |
| 5,178,163 | 1/1993 | Yewer, Jr. | 602/19 X |
| 5,388,274 | 2/1995 | Glover et al. | 2/338 |

FOREIGN PATENT DOCUMENTS 187933  2/1964  Sweden ........................ 182/3

Primary Examiner—Richard J. Apley
Assistant Examiner—John Mulcahy

[57] ABSTRACT

A waist belt for weight lifting incorporates a strap ratchet and nylon strap for tightening the belt. The waist belt includes a heavy leather belt and a nylon strap, both with first and second ends. The strap ratchet is secured on the belt loop near the first end of the belt. The first end of the nylon strap is attached to the strap ratchet. The nylon strap is sewn to the belt until a quarter of the leather belt remains at the second end of the belt. The second end of the nylon strap hangs free at the second end of the leather belt. The second end of the leather belt is placed through the middle of the belt loop, gripping support loops as necessary. The second end of the nylon strap is placed through the strap ratchet nylon strap tightening mechanism. The belt is now tightened by gripping the strap ratchet's handle and ratcheting by hand for desired tightness. Belt is quickly unbuckled by pulling up and holding strap ratchet's nylon strap release mechanism and pulling fully open strap ratchet's handle.

7 Claims, 2 Drawing Sheets

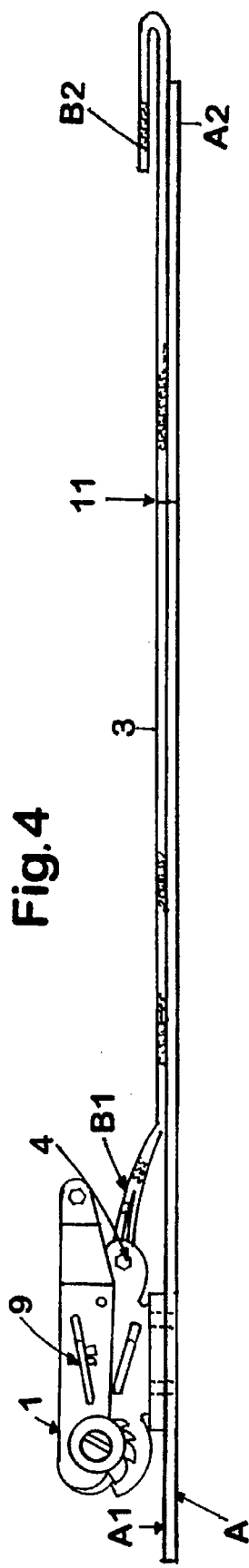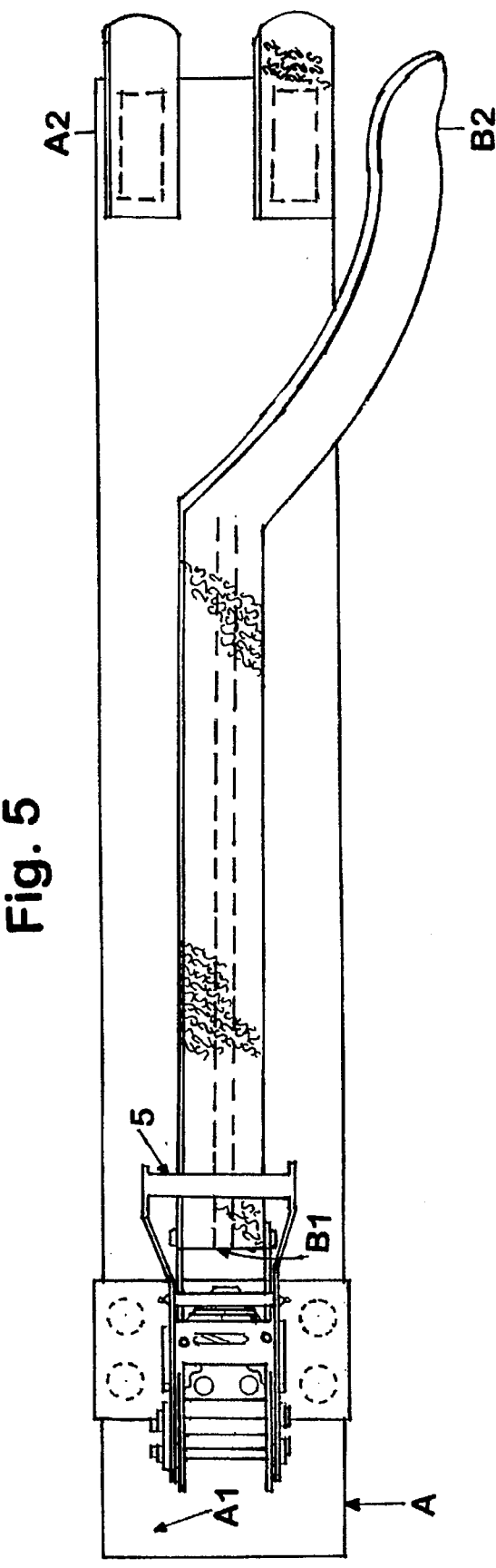

WEIGHT LIFTER'S BELT INCORPORATING STRAP RATCHET AND NYLON STRAP

BACKGROUND OF THE INVENTION

1. Field of the Invention

This invention relates generally to belts, and more specifically, to a weight lifter's belt incorporating a strap ratchet and nylon strap for tightening the belt.

2. Description of the Prior Art

For a variety of sports including weight lifting, and powerlifting, weight lifter's frequently wear a waist belt to provide additional support to their bodies in order to lift more weight and to prevent injury. During the execution of weight lifting, all physical energy is applied by the weight lifter, consequently it is the lower abdominal area of the torso which requires support and containment. Without the use of a weight lifting belt, weight lifters would not be able to lift their maximum loads. Traditional weight lifting belts are made of heavy leather and configured like standard men's dress belts with a buckle and tongue engaged in a hole for fastening the ends. When desired by the wearer the buckle and tongue are brought together, tightened and fastened as desired. Recreational weight lifting belts can be of any size and thickness. However, the size of weight lifting belts used in US and international sanctioned competition are governed by the rules of various federations. Typically, weight lifting belts used in competition are approximately four inches wide and one-quarter of an inch thick.

Weight lifting belts must be secured very tightly for the wearer to obtain maximum benefit and support from the belt. Because of the large size and thickness required of competition weight lifting belts, weight lifter's typically find it difficult to properly tighten their weight lifting belts. Consequently, it is not uncommon for weight lifter's to ask for help in tightening/buckling and loosening/unbuckling their belts.

Accordingly, it is an objective of the herein invention to provide a weight lifting belt which can be sufficiently tightened, fastened, and unfastened by the wearer alone in order to provide himself/herself with proper support, and which belt can be easily and quickly removed by the wear alone.

It is another objective of the present invention to provide a weight lifting belt which can be incrementally tightened in fractions of an inch so that variations in personal preference for adjustments in tightness can be made by the wearer alone.

It is another objective of the present invention to provide a weight lifting belt which can be quickly and easily release. This characteristic of a weight lifting belt is especially important for safety reasons, and for speed reasons. In case of injury it may be necessary to quickly unfasten and remove a weight lifting belt from a wearer. During weight lifting competition there are specific time intervals between when weight lifters must perform their lifts that are strictly enforced, thus competitors need to quickly remove weight lifting belts and other gear as quickly as possible to prepare for their next lift.

SUMMARY OF THE INVENTION

The present invention relates to a waist belt for weight lifting incorporating a strap ratchet and nylon strap arrangement for tightening the belt. The present invention replaces prior art buckles and the like which primarily are restricted to the placement of holes in the leather belt for adjusting belt tightness. With the present invention tightening the belt is achieved by placing the second end of the leather belt through the belt loop, then placing the nylon strap through the strap ratchet nylon strap tightening mechanism, and next by grasping the strap ratchet's tightening handle and ratcheting the belt tight. The strap ratchet tightens the belt in fractions of an inch, until the wearer feels the most secure and comfortable. For disengaging the belt, the wearer fully opens both the nylon strap loosening mechanism and the strap ratchet handle to the fully open position. Then by pulling on the nylon strap and/or pushing out the abdominal muscles the belt fully unbuckles.

The present invention is one embodiment thereof which the strap ratchet is fastened to the weight lifting belt loop. The weight lifting belt loop is fastened to the leather belt at approximately 4 to 5 inches from the first end of the leather belt. A nylon strap is attached to the strap ratchet's nylon strap connection point. The nylon strap is sewn by stitching to the leather belt in the center of the belt itself, and sewn up to approximately three quarters of the way to the second end of the leather belt. The remainder of the nylon strap hangs free. At the second end of the leather belt two short nylon strap handles are attached to the leather belt which are used to assist the wearer in tightening the belt.

For fastening the belt a wearer of the present invention puts the belt around himself and places the second end of the leather belt through the belt loop. The wear then places the nylon strap through the strap ratchet's nylon tightening mechanism. Then by simultaneously pulling the short nylon handles of the second end of the leather belt and by ratcheting the strap ratchet, the belt tightens in fractions of an inch. Once the belt is tightened as desired, place the strap ratchet handle in the closed position.

For unfastening the belt a wearer of the present invention pulls, to the open position, the strap ratchet's nylon loosening mechanism and pulls the strap ratchet handle to its full open position. These two actions unlock the nylon strap. Now the nylon strap is loose and can be easily loosened. Furthermore, a wearer could push out with their abdominal muscles to help loosen the belt.

BRIEF DESCRIPTION OF THE DRAWINGS

FIG. 4 is a side view of the belt.

FIG. 5 is a top view of the belt.

DETAILED DESCRIPTION OF THE PREFERRED EMBODIMENT

Figure 1:
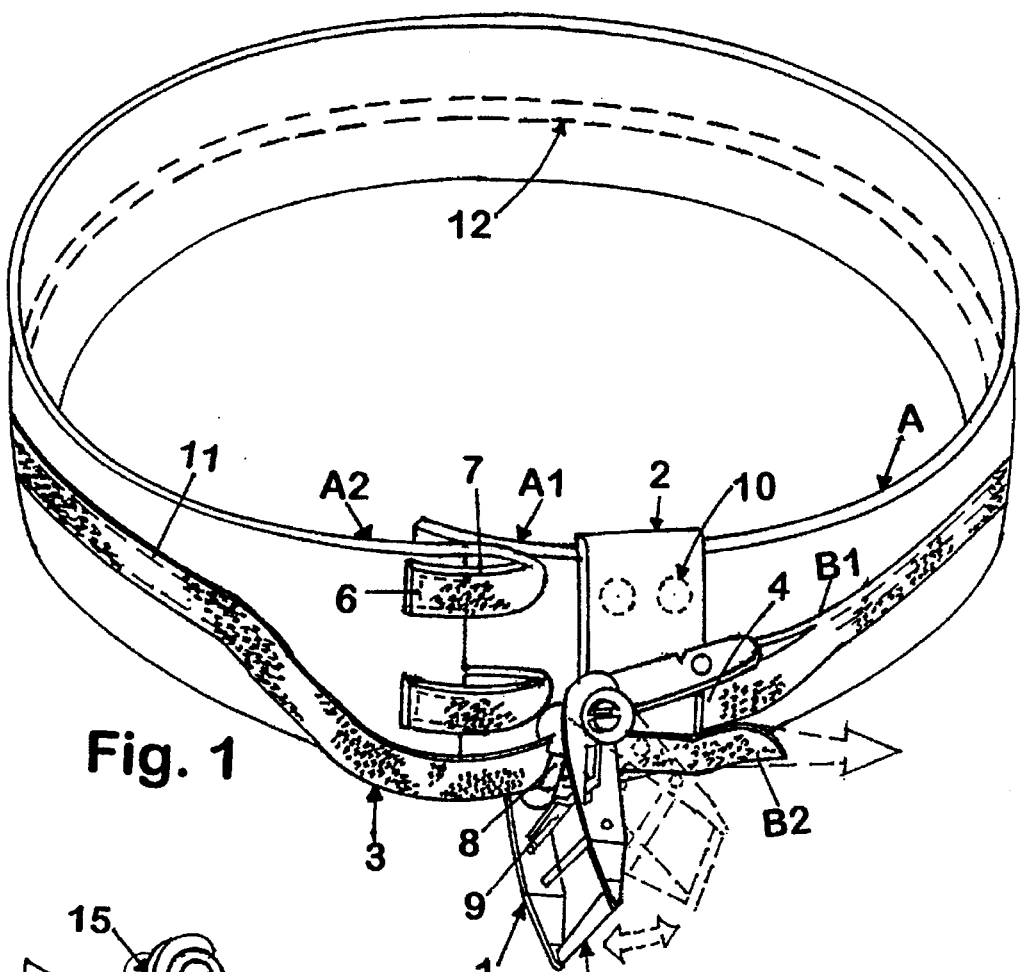
FIG. 1 is a perspective view of a weight lifting belt incorporating a strap ratchet and nylon strap arrangement according to the herein invention.

Referring now to the drawings, FIG. 1 illustrates a waist belt for weight lifting which includes a leather belt A with first end designated A1 and second end designated A2. And a nylon strap with first end designated B1 and second end designated B2. For recreational purposes the leather belt A can be any size, but for sanctioned weight lifting competitions the leather belt A must not exceed approximately four inches in width and one-quarter of an inch thick.

As show in FIG. 1 strap ratchet 1 is not fully attached to the belt loop 2 so that belt loop rivets can be revealed in the drawing. Nonetheless, the strap ratchet is attached to belt loop 2 and ratchet is depicted halfway open. The strap ratchet 1 can be welded, brazed, sewn, glued or riveted to the belt loop 2. The belt loop can be made from metal plastic or leather. The first end B1 of the nylon strap 3 is attached to the strap ratchet 1 at the nylon strap attachment point 4. The nylon strap 3 is sewn by stitching to the center 12 of leather belt A until three quarters of the way 11 to the second end A2 of leather belt A. The remainder of nylon strap 3 hangs free. Two short nylon strap handles 7 are sewn by stitching 6 to the second end A2 of leather belt A. The nylon strap handles are used by the wearer to help pull the second end of the belt through the belt loop.

FIG. 1 also depicts the nylon strap second end B2 placed through the strap ratchet's nylon strap tightening mechanism 8. For tightening the strap ratchet handle 5 is ratcheted back and forth as depicted by the arrow until the wear is satisfied. To loosen the wearer pulls and holds the nylon strap loosening mechanism 9, grasps the strap ratchet handle 5 and fully opens it (those two operations can easily be accomplished with one hand), and pulls the nylon strap out of the nylon strap tightening mechanism.

Figure 2:
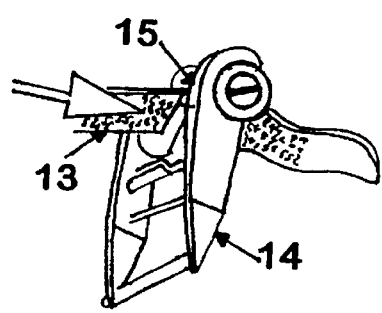
FIG. 2 is a close-up perspective view of the nylon strap being placed through the strap ratchet's nylon strap tightening mechanism.

FIG. 2 shows a close up view of the nylon strap tightening mechanism 15. This view depicts the nylon strap 13 placed through the hole in the mechanism. It also depicts a partial view of the strap ratchet.

Figure 3:
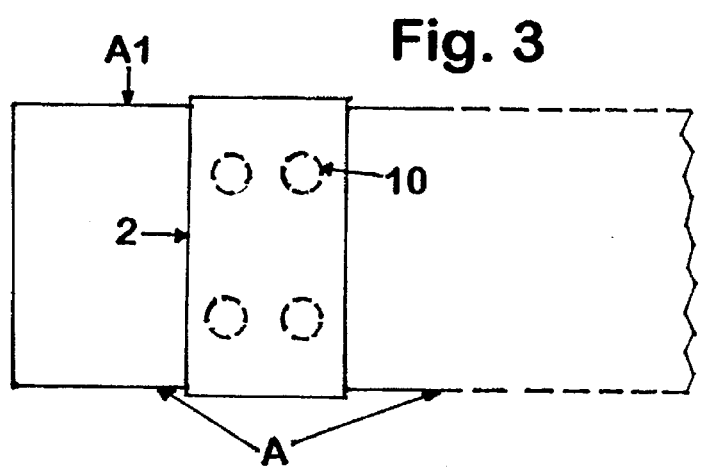
FIG. 3 is a partial top view of the first end of the leather belt and belt loop. The belt loop is attached to the leather belt by four rivets. The strap ratchet is removed from the belt loop.

FIG. 3 depicts a cut off view of the leather belt A first end A1, belt loop 2, and rivets 10 to secure belt loop to leather belt. This is a top view and depicts the belt with the strap ratchet and nylon strap removed.

FIG. 4 depicts a side view of the present invention. This view further clarifies the interrelationship of the various parts of the herein invention. The strap ratchet 1 is attached to the belt loop which is attached to the leather belt A. The first end of the nylon strap B1 is attached to the strap ratchet at the connection point 4. The nylon strap 3 is sewn to the leather belt three quarters of the way 11 to the end of the second end A2 of the leather belt.

FIG. 5 depicts a top view of the present invention. This view further clarifies the interrelationship of the various parts of the herein invention. The ratchet handle 5 is clearly visible in this view. The first end B1 of the nylon strap is attached to the strap ratchet connection point and is sewn to the leather belt A in the center until three-quarters of the way to the second end A2 of the leather belt. The remainder of the second end of the nylon strap B2 hangs free.

I claim:

1. A support belt for weight lifting, other sports and activities comprising:

a belt having a belt loop proximate one end thereof for receiving the other end;

a strap ratchet secured to the belt loop and having a release mechanism;

a strap having one end secured to the strap ratchet, an intermediate portion of the strap being secured to the belt, the other end of the strap being free;

whereby the belt may be donned by placing the belt about the waist with the other end of the belt through the belt loop, engaging the free end of the strap to the strap ratchet and incrementally tightening the strap therewith.

2. The belt of claim 1, further comprising a short strap attached to the other end of the belt for gripping by the wearer when pulling the other end of the belt through the loop.

3. The belt of claim 1 wherein the strap ratchet incrementally tightens the belt in fractions of an inch.

4. The belt of claim 1 wherein the strap ratchet is secured to the belt loop by rivets and/or welding or sewing or gluing.

5. The belt of claim 1 wherein the belt loop is metal, leather or plastic.

6. The belt of claim 1 wherein the belt is leather.

7. The belt of claim 1 wherein the strap is nylon.

* * * * *